United States Patent [19]

Pierpaoli et al.

[11] Patent Number: 4,540,574
[45] Date of Patent: Sep. 10, 1985

[54] WATER SOLUBLE FRACTION CAPABLE OF CONTROLLING THE IMMUNE REACTIONS OF A HOST AGAINST ALLOGENIC CELLS OR TISSUE, THE PHARMACEUTICAL COMPOSITIONS CONTAINING SAID FRACTION AND A PROCESS FOR PREPARING THE LATTER

[75] Inventors: Walter Pierpaoli, Ebmatingen; Georges Maestroni, Benglen, both of Switzerland

[73] Assignees: Cellena (Cell Engineering) A.G., Bmatingen, Switzerland; Choay S.A., Paris, France

[21] Appl. No.: 279,994
[22] PCT Filed: Nov. 21, 1980
[86] PCT No.: PCT/EP80/00136
§ 371 Date: Jul. 2, 1981
§ 102(e) Date: Jul. 2, 1981
[87] PCT Pub. No.: WO81/01367
PCT Pub. Date: May 28, 1981

[51] Int. Cl.³ .............................. A61K 35/28
[52] U.S. Cl. ..................................... 424/95
[58] Field of Search ........................... 424/95

[56] References Cited

U.S. PATENT DOCUMENTS 3,526,697  9/1970  Livingston ............................ 424/95
3,676,551  7/1972  Thuillier .............................. 424/95

*Primary Examiner*—Sam Rosen
*Attorney, Agent, or Firm*—Weiser & Stapler

[57] ABSTRACT

Water soluble biologically active fraction obtainable from the physiologically inter-cellular medium bone-marrow and process for preparing said fraction and the pharmaceutical compositions containing said fraction. The characteristics are notably the following: it is substantially free of the inhibitors having molecular weights lower than 30,000; it is lyophilizable without loss of biological properties; it exhibits the biological activities in the form of a solution having a pH of at least 7; it stimulates H-thymidin incorporation by bone-marrow cells in vitro and in vivo; the water soluble fraction is capable of controlling the immune reactions of a host against allogenic cells or tissue.

35 Claims, 1 Drawing Figure

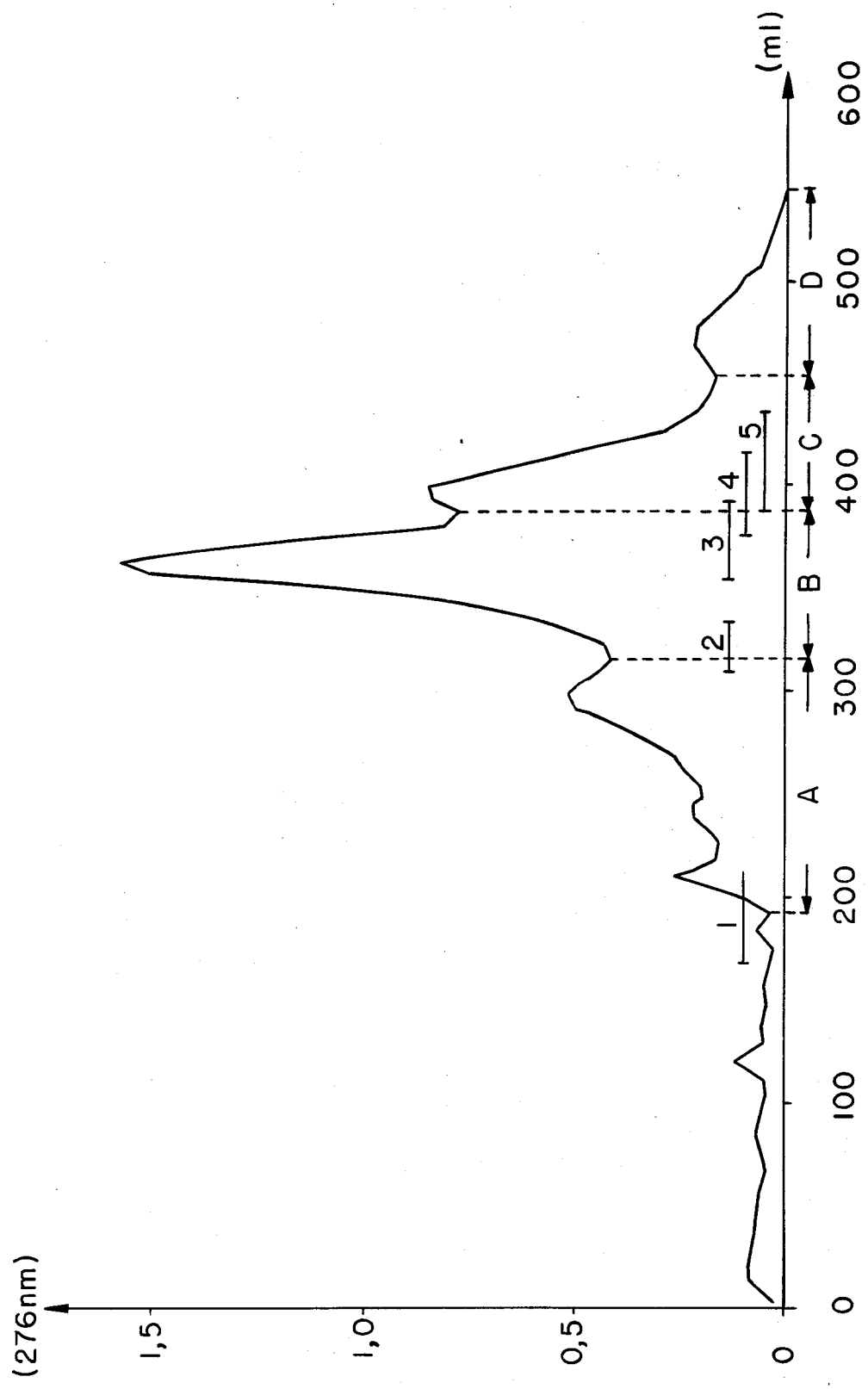

WATER SOLUBLE FRACTION CAPABLE OF CONTROLLING THE IMMUNE REACTIONS OF A HOST AGAINST ALLOGENIC CELLS OR TISSUE, THE PHARMACEUTICAL COMPOSITIONS CONTAINING SAID FRACTION AND A PROCESS FOR PREPARING THE LATTER

The invention relates to a water soluble fraction from bone marrow having biological activities including that of controlling the immune reactions of a host against allogeneic cells or tissue, particularly host versus-graft reaction (HVGR) and so-called graft versus-host reaction (GVHR) in transplantation of allogeneic incompatible bone marrow, of promoting engraftment of allogeneic marrow in vivo and of protecting the host against irradiation and the consequences of irradiation.

It has already been published that viable bone marrow cells were capable of controlling immunological reactions (HVGR and GVHR) ensuing when immunogenetical different bone marrow is transplanted into a lethally irradiated host (immunity). More particularly, it has already been found that bone marrow cells were capable of facilitating engraftment of foreign cells or tissue (allogeneic or xenogeneic in a host) when administering them to said host according to a determined protocol or regimen including a total body irradiation procedure, the latter being aimed at destroying the host's own immune system and at facilitating the substitution for it of an immune system of foreign origin.

More particularly, it has been found that the treatment of mice, which comprises administering to them rat bone marrow cells, then subjecting them shortly thereafter to lethal total body irradiation (TBI) and subsequently readministering new bone marrow cells, resulted in remarkable protection of said mice against radiation injury, also, when the bone marrow cells administered after TBI were of xenogeneic origin (i.e. rat), facilitation of marrow engraftment and induction of a persisting xenogeneic (rat) chimerism in said mice occurred ("A new pre-irradiation conditioning regimen which protects against radiation injury and facilitates engraftment of xenogeneic bone marrow"-Walter Pierpaoli & Georges J. M. Maestroni, Scand. J. Haematol. (1979), 22, 165–172.

The operational procedure preceding TBI was, and will hereafter be in relation to the invention, be designated by "preconditioning" while the designation "post-conditioning" referred to will also hereafter refer to the administration of material of bone marrow origin after TBI.

On utilizing the model of xenogeneic (rat to mouse) marrow transplantation, it was established that the critical factors for success included a sufficient number of viable bone marrow cells before and after TBI, the timing and the route of inoculation; each of these had to be correctly poised to assure protection against secondary disease, long term survival and the development of chimerism.

The present invention stems from the discovery that the viable marrow cells were exerting this strikingly favorable effect via synthesis and/or secretion, in the host, of components facilitating engraftment of the transplanted incompatible marrow after lethal TBI.

Particularly, it has been found that the abovesaid favorable effect can be attributed to a water-soluble biolocigally active fraction obtainable from the physiological inter-cellular medium of bone marrow of any mammalian animal, particularly, after separation therefrom of the bone marrow cells themselves.

This discovery was all the more unexpected as the physiological inter-cellular medium (bone marrow supernatant SN) as such does not exhibit substantial activity, unless special care is taken to avoid inactivation of the biologically active fraction. Reproducible activity in a testing system as hereabove defined and as said biologically active fraction tends to be inactivated when the pH is neutral or tends to fall below 7.0 and contains both inhibitors and activators of bone marrow functions.

The water-soluble biologically active fraction according to the invention which is obtainable from the physiologically inter-cellular medium of bone marrow has the following characteristics:

it is substantially free of inhibitors which have molecular weights essentially lower than about 30 000;

it is lyophilizable without loss of biological properties;

it exhibits the hereafter defined diological activities in a solution having a pH of at least 7, preferably from 7.2 to 7.6;

it stimulates $^3$H-thymidine incorporation by bone marrow cells in vitro and in vivo;

it allows the engraftment of allogenic bone marrow and induces persistent chimerism in previously lethally irradiated animals, as well as survival of the latter;

the activity is not species-specific;

its activity is destroyed by heating at 70° C. for 30 mm, and its UV spectra shows a peak of absorption at 20 280 nm.

Further preferred fractions according to the invention are also substantially free of the components contained in the physiological inter-cellular medium of bone marrow which have both molecular weights less than 100 000 and consist of inhibitors of the biological activity, as hereabove defined, of the fraction according to the invention. Particularly a preferred fraction is substantially free of those inhibitors that are filtrable through a filtration system, such as a microporous membrane, allowing the separation and removal of components having molecular weights essentially lower than 100 000, from said physiological inter-cellular medium, or a buffered or a saline solution thereof.

It follows from the preceding definitions that, apparently, the whole physiological inter-cellular medium of bone marrow contains inhibitors of the activity of the biological fraction according to the invention, which seem to have molecular weights not exceeding about 30 000.

The invention also contains a process for obtaining said biological fraction from bone marrow, which comprises the steps of separating and recovering the physiological inter-cellular medium from the bone marrow cells, then further separating from said inter-cellular medium, if need be in the form of a diluted solution in a physiological, buffered or saline solution, those components which are filtrable through a filtration system, more particularly, a microporous membrane, allowing the separation of components having molecular weights not greater than about 30 000, preferably not above 100 000, and then recovering the biologically active fraction which is free from the abovesaid components of lower molecular weights.

Preferably, the pH of the medium is maintained at all times at a value not lower than 7.0, preferably from 7.2 to 7.6.

For carrying out the separation of the physiological inter-cellular medium from the bone marrow cells, the bone marrow is preferably suspended beforehand in a physiological solution, particularly a saline solution or a buffered solution whose pH has been adjusted between 7.2 and 7.6 and, if need be, the cells are separated after controlled gentle dissociation of the bone marrow tissue so as to avoid possible destruction of the cellular material.

An advantageous buffered solution consists of Hanks' medium or Earle's medium pH 7.4.

The temperature under which all the above operations may be carried out is preferably below ambient, more preferably between 0° and 5° C.

This procedure thus enables a biologically active fraction to be obtained, which is capable of controlling the immune reactions under conditions substantially the same as those which have been mentioned above in connection with whole bone marrow cells, as will be hereinafter illustrated.

The activity of the biological fraction of the invention is not species-specific. It is fully devoid of toxicity.

The fraction of the invention is also characterized by the ability that it has to react immunologically with antibodies formed in an heterologous host against the fraction as obtained by the process herein defined (hereafter designated as MRF).

In order to investigate the organ and tissue specificity of marrow regulating factors (MRF), the following technique can be adopted and is hereby described in its essential lines.

Sheep or goats are repeatedly injected with human or rabbit MRF intramuscularly (four times at four-week intervals). One week after the last injection, blood is collected and serum separated, divided into aliquots and frozen. The animals are then injected once more and serum is collected one week afterwards. The quantity of MRF injected each time is 10 mg/sheep. MRF is dissolved in saline solution from the lyophilized state, prior to injection.

Aliquots of the sheep anti-rabbit MRF and sheep anti-human MRF are repeatedly absorbed with washed and packed rabbit thymus and spleen cells, in order to remove the antibodies which are not specifically directed against MRF but against other, different and organ-specific antigens. Antibodies against MRF are determined by the direct precipitin assay or by the passive haemagglutination technique with formalin-treated and antigen (MRF)-coated sheep red cells. The combination of these serological techniques and of radioimmunoassay (RIA) with radioiodinated ($^{125}$I) MRF allows to establish:

1° the presence of anti-MRF antibodies and their titer;

2° the presence of organ-specific (particularly bone marrow) antibodies;

3° the possible cross-reactivity of human and rabbit MRF (agglutination-inhibition test);

4° the presence of MRF in tissue extracts or preparations of unknown origin (immunological) identification), and 5° the possible organ-specificity but not biological species-specific activity of human and rabbit MRF (e.g. rabbit MRF is active on human BM cells and human MRF is active on rabbit BM cells).

In summary, serological tests and RIA will allow the identification on MRF as a possible unique combination of substances with organ-specificity, non-species specificity of biological activity.

The invention also concerns pharmaceutical compositions containing such fraction in association with a pharmacological vehicle so as to enable the administration to a host, i.e. by parenterally, such as the intravenous route.

The invention will be further illustrated in a non-limitative manner by the following description of a preferred mode of extraction of a biological active fraction according to the invention from the bone marrow of animals, such as mice, rats, rabbits, sheep, and of their biological properties.

The saline solution of the abovesaid physiological inter-cellular medium will be hereafter referred to as "bone marrow supernatant", and the biologically active fraction of the invention as "marrow regulating factor" (MRF).

I-DESCRIPTION OF THE METHOD USED FOR PREPARATION OF BONE MARROW SUPERNATANTS (SN) FROM WHICH THE MARROW REGULATING FACTOR (MRF) IS EXTRACTED

Young adult donors (groups of ten, male or female rabbits between 1.5 and 2.0 kg body weight) were killed by cervical dislocation. The long bones were isolated and put into refrigerated TC 199 or saline (NaCl) 0.9%). The bones were then cut at the extremities and TC 199 or saline solution was flushed repeatedly through the bones to expel all the marrow, including fat tissue and connective tissue and all that make up the inter-cellular medium of the bone marrow. The material (clots of marrow, fat, other tissues) was then dissociated by using a large syringe without needle, delicately aspiring and expelling the suspended material which was always kept in melting ice, until no cell aggregates were visible. The number of cells in the suspension ranged between 50 and $100 \times 10^6$/ml of SN. At this stage, The whole initial suspension of material was centrifuged in a refrigerated centrifuge at 5° C. for 30 minutes at $10,000 \times g$ and the fat condensed at the top of the tubes was eliminated by aspiration. The rest of the supernatant was collected in plastic containers and frozen immediately at $-30°$ C. The cells were discarded. All this preparatory work was carried out under sterile conditions. SN is intended to be the original suspension medium in which the bone marrow cells were dissociated and suspended. The pH of all cell suspensions, and preparations of SN was kept or corrected at 7.2 to 7.5.

Preparation of MRF from rabbit bone marrow supernatant (SN)

After thawing the SN, it was centrifuged for 20 minutes at $40\,000 \times g$ in a refrigerated centrifuge to remove all possible particles and precipitate. The SN was then passed over a Diaflo XM 100 filtration membrane (MW: cut off 100 000); Amicon Co., Oosterhout, Holland, using an Amicon Model 202 Cell, to eliminate the fraction containing separated compounds having apparent molecular weights less than 100 000. In some experiments the latter fraction was then passed over a Diaflo XM 30 filtration membrane (MW: cut off 30 000) in order to further remove components which have molecular weights less than 30 000. An equal volume of water was used in each experiment to wash the material which did not pass through the filter. The materials remaining on the filters were withdrawn with a syringe and lyophilized.

The different fractions tested hereafter were designated as follows:

"MW>100 000" is the MRF fraction freed from components having molecular weights less than about 100 000;

"MW>30 000" is the fraction freed from components having molecular weights less than about 30 000;

"MW<100 000" is the fraction freed from components having molecular weights above 100 000;

"MW<30 000" is the fraction freed from components having molecular weights above 30 000.

These different fractions are referred to in the tables hereafter under the above designations.

The biological activity of the MRF fractions as measured by activation or inhibition of $^3$H-thymidine incorporation by bone marrow cells in vitro is made inactive by lowering the pH below 7.0 and by heating at 70° C. for 30 minutes.

In an another experiment, 150 mg of the material "MW>100 000" were dissolved in 5 ml of 0.1M N-ethylmorpholine acetate buffer having a pH 7.4.

After centrifugation (10 minutes, 40 000 g) an insoluble pellet was obtained and washed with 2 ml of the same buffer. The supernatant+washings (7 ml) were mixed and introduced on a column (2.5 cm×90 cm) of a polyacrylamidagarose gel beads commercialized under the designation ULTROGEL AcA 34 that has been equilibrated with the same 0.1M pH 7.4 N-ethylmorpholine acetate buffer.

The gel filtration took place under the following conditions:
flow rate: 13,5 ml/hr
fractions volume: 3 ml
temperature: +4° C.

The pattern obtained is shown in FIG. 1, which is representative of the contents of the successively eluted volumes (in ml) as measured in UV spectrophotometry (absorbance at 276 nm).

Four fractions were obtained as indicated, respectively fractions:
A (27 mg),
B (74 mg),
C (18 mg),
D (3.6 mg).

Total yield (by weight): 82%

The horizontal bars numbered 1, 2, 3, 4 and 5 shown on the FIGURE, correspond to MW markers, respectively:
1: blue dextran (MW of about 2,000,000),
2: bovine serum albumin (MW of about 67,000),
3: ovalbumin (MW: 47,000)
4: carbonic anhydrase (MW; 30,000)
5: chymotrypsinogen (MW: 25,000)

Fraction B of FIG. 1 was also found to be highly active in the tests hereafter illustrated and which bring forth the activity of "fraction of MW 100,000".

Fraction B comprises components which can roughly be stated to be formed of components having molecular weights ranging from about 40,000 to about 70,000.

II-BIOLOGICAL ACTIVITIES

1° Materials and methods

Animals: the animals used were mice, which have been bred under specific pathogen-free conditions and then maintained, as adults, under strictly standardized and controlled hygienic conditions. However, no special precautions were taken to avoid pathogenic bacteria or viruses. No antibiotics were administered via drinking water either before or after irradiation.

Donors or recipients of bone marrow were inbred young adult (8-12 weeks old) C578L/6, DBA/2 and C578LxA/J F1 hybrid mice. The rabbits used were an outbred Swiss strain, 1.5 to 2 kg body weight. They were used as donors of xenogeneic marrow for preparation of supernatant (SN) from which the fraction containing marrow regulating factors were separated. This fraction is hereafter referred to as MRF.

Preparation of bone marrow cell suspensions

Suspensions of bone marrow cells were freshly prepared 2-3 hours before inoculation. Mice were killed by cervical dislocation, the long bones (humeri, tibiae and femurs) were isolated and cut at the extremities. Ice-cold TC 199 medium was flushed repeatedly through the cavities by a syringe with a needle fitting the bone size. The pooled marrow was gently dispersed by a needleless syringe and filtered through the gauze. The cells were then washed 2-3 fold by low speed centrifugation, using ice-cold TC 199 medium. The final cell suspensions were adjusted to the desired number and volume. Quantities varying from 20 to 40×10$^6$ cells per donor mouse could be harvested. The cells were administered in a volume of 0.9 ml per mouse, i.v. Trypan-blue exclusion tests showed that over 95% of the cells were viable just before their inoculation.

Irradiation

A dose of 850 to 900 rads total body irradiation 5(TBI) was given to the recipients depending on the known strain sensitivity to irradiation (5). This dose led to death of all untreated mice within 8-15 days. The irradiation apparatus was a Cobalt Gammatron 3 (6 000 Curie). Field size was 30×30 cm. main focus distance was 90 cm. No filters were used.

Transplantation of allogeneic marrow (a) Pre-conditioning regimen

When this regimen was adopted the mice were injected i.v. 1.5 to 2.0 hours before irradiation with 1.0, 2.5 or 5 mg of rabbit MRF. The lyophilized material (fraction with MW 100,000) was dissolved in TC 199. The vlume injected was 0.5 ml. Controls were injected with cells or medium without cells or medium without MRF.

(b) Post-conditioning regimen

The mice were injected 24 hours after TBI with 35 to 37×10$^6$ washed bone marrow cells. Depending on the experimental plan the cells were injected alone or suspended in the medium containing the fractions of the MRF. The cells were resuspended in the medium (TC 199, pH 7.4) containing MRF shortly before i.v. inoculation. In some tests the cells and the MRF were injected separately (Table 1).

Tests for Chimerism (a) Hemoglobin migration pattern

At monthly intervals after TBI, all mice were individually tested for chimerism of the erythroid cell line. A few drops of blood were taken from the retroorbital plexus, suspended in heparinized saline and washed repeatedly. The washed blood cells were hemolyzed in 1:5 cell water volume. The pattern of hemoglobin migration was examined by cellulose-acetate electrophoresis. The strips were stained with Amido Slack. Engraftment of the donor erythropoietic line corresponded to complete chimerism as confirmed by skin grafting.

(b) Skin grafts

In the situation of cross-transplantation of bone marrow from or into C57BL/6 or DBA/2 donor/recipient, donor skin was grafted on groups of allogeneic marrow recipients. Grafting was by conventional technique; the corsets were removed after 8–10 days and the viability of the grafts was checked daily. The graft was considered as rejected when the first signs of infiltration, oedema and induration appeared. They were considered as accepted only when none of these signs were discernible and luxuriant hair grew on the transplanted skin.

Incorporation of $^3$H-thymidine by bone marrow cells in vitro

6-$^3$H-thymidine, 27 Ci/mM was purchased from the Radio-Chemical Center, Amersham, England. Washed bone marrow cells freshly taken from adult C57BL/6 mice were incubated for 1, 2 and 3 hours in sealed tubes in the presence of 2 $\mu$Ci of $^3$H-thymidine. Samples were in triplicate. Each tube contained $2 \times 10^6$ washed bone marrow cells suspended in 1 ml of medium TC 199, or in TC 199 with 200 $\mu$g of the ultrafiltration fractions of the original supernatant of rabbit bone marrow cell suspensions (see above preparation of MRF). The pH of the medium was adjusted to 7.5. After 1, 2 and 3 hours of incubation, 0.1 ml of 10% sodium dodecyl sulphate (SDS) was added to each tube. After a vigorous shaking, DNA was precipitated at 4° C. for 15 minutes by adding to each tube 1 ml of 10% trichloroacetic acid (TCA). The precipitate was collected on Whatmann GF/C glass fiber filters and washed with 5% TCA and absolute ethanol. The filters were dried and the activity was measured in a LKB-Wallac 81 000 liquid scintillation counter.

The results of the different tests run according to the invention are presented in the tables hereafter.

The comment under each table provides the information appropriate for the understanding of the experimental conditions, to the extent where it does not appear in the present description.

The "ratio MRF/BM cells", where appropriate, is the ratio of the number of cells which in the bone marrow of origin accompanied the amount of MRF used in the experiments concerned to the number of cells contacted with said amount of MRF in the solvent also identified in the corresponding column.

The experimental conditions appear in the headings of the different tables.

In tables 1–5, there is indicated in the right hand column the operational conditions, particularly, the nature of the components contacted with one another.

In table 7, the numbers, if any, in the sub-columns under the headings "h$^-$" and "h$^+$" indicate the times in hours of injection of the MRF before and after TBI respectively. In the sub-column with the sub-heading "No of BM cells ($\times 10^6$)" under the general heading "Post-conditioning" reference is made to the number of bone marrow cells injected together with the corresponding amount of MRF, if any, in the left hand-side neighboring sub-column.

TABLE 1

The table shows that the activity of the MRF in enhancing $^3$H-thymidine incorporation is dependent on the pH of the incubating medium (compare lines 1, 2 and 3 which are the controls with lines 4, 5 and 6).

It also shows that the activity is not species-specific (compare lines 2 and 5 with 7 and 8). Lines 5 and 7 show that rat SN is active on rat bone marrow cells as well as on mouse cells.

TABLE 2–TABLE 3

The experiment reported in Table 2 was conducted using whole supernatant (SN), while the experiment reported in Table 3 was conducted using ultrafiltrated SN (MRF) on Amicon Diaflo Membrane 10,000 and 30,000. The result of each case was compared to the one obtained with TC 199 medium.

Table 2 shows that the whole supernatant (SN) induces less $^3$H-thymidine incorporation than the reference medium TC 199 (lines 1 and 3). "Fraction above 30,000" stimulates the $^3$H-tymidine incorporation while "Fraction below 30,00" inhibits the incorporation (lines 1 and 3 and line 2). Furthermore, the "Fraction below 100,000" shows no effect on incorporation (line 4).

Thus, one can see that the SN also contains inhibitors which prevent the stimulation of $^3$H-thymidine incorporation by the activating factor.

This experiment shows that inhibitory fractions and stimulating fractions can be separated by the ultrafiltration of SN on Amicon Diaflo Membrane 100,000.

Furthermore, experiment 2 of Table 2 shows that the action is not due to a non-specific mitogenic effect of heterologous protein (rabbit in that case) as BSA does not affect the incorporation (line 2) over that of TC 199 (line 3).

TABLE 4

The experiment allows for the comparison of the respective actions of the MRF fraction ("MW above 100,000") before and after treating at 70° C. for 30 minutes.

The results presented in Table 4 show that after 1, 2, as well as 3 hours, the incorporation is much lower for the heated product. Thus, heating seems to destroy the stimulating factor.

TABLE 5

Ultrafiltrated MRF fractions "above 100,000" are here compared with fractions "below 30,000" and "below 100,000" for their stimulation of $^3$H-thymidine incorporation in vitro.

Here again one sees that only the fraction above 100,000 MW is able to stimulate the incorporation of thymidine by bone marrow cells.

TABLES 6 AND 7

In these two experiments, the MRF and the thymidine are inoculated intravenously into groups of mice. The animals receive I.V. 500 $\mu$g or 1 mg of the fraction and 2 or 4 $\mu$Ci of thymidine in 0.1 or 0.5 ml of saline. Mice are sacrificed 1 and 2 hours after the injection.

Comparisons are made with control groups of mice treated with BSA and thymidine or with "heated" MRF fraction and thymidine.

Bone marrow of one tibia is collected and adjusted at 2, $10^6$ cells per ml and processed as described in the in vitro experiment.

Conclusion: the "fraction above 100,000" causes, also in vivo an, increase of the incorporation of $^3$H-thymidine by mouse bone marrow cells.

This experiment confirms that the activity is not due to an heterologous protein (table 7) and that it is destroyed by heat (table 6).

2° Pharmacological activity-Bone marrow transplantation

The bone marrow transplantation is a therapy which can be considered for hematopoietic malignant disorder, for instance leukemia, aplastic anemia, etc. Until now such transplantation has never been achieved when genetical incompatibility between donor and recipient is present.

The following experiments show that MRF allows engraftment of bone marrow between incompatible donor and recipient by influencing positively the engraftment of the foreign marrow.

Two different models have been used: one where animals are totally genetically incompatible, DBA 6 donors and C57BL/6 recipient, see table 8, and one with semi-compatible donors and recipients: C57BL/6 donors and hybrid C57BL/6XA/J F1 recipients (see table 9).

The purpose of the experiment was to achieve persisting BM allogenic chimerism. The criteria for the success (persistent chimerism) are:

migration pattern of hemoglobin showed by cellulose acetate electrophoresis. Donor and recipient have genetically different patterns of hemoglobin. Chimeric mice carry the hemoglobin of the bone marrow donor;

skin grafting: permanent chimera accepted permanently by skin graft from the marrow donor;

another criteria for successful engraftment of allogeneic marrow is health condition and survival without appearance of secondary disease under conventional conditions (so-called GVHD or Runting disease).

Animals were treated as described below with ultrafiltrated MRF fraction dissolved in TC 199-0.5 ml.

TABLE 8

This table reports the results of attempts to produce survival of a first "strain of mice successively pre-conditioned", then irradiated and finally post-conditioned and injected with bone marrow of another strain of mice known to be normally genetically totally incompatible at the H2 locus with the first one. The experiment was carried out as follows.

Recipients are injected intravenously 1 to 2 hours before irradiation with the MRF fraction, they they are lethally irradiated and 24 hours after irradiation they receive I.V. washed bone marrow cells of the donor suspended in a medium containing the MRF fraction.

The pre- and post-conditioning with the MRF fraction "above 100,000" under the above condition allowed for good survival and persistent chimerism as demonstrated by hemoglogin patterns and permanent take of skin graft (from DBA/2 donors in the surviving animals).

The animals surviving after 6 months are in perfect conditions and show no signs of secondary disease. It is worth while noting that full chimerism is obtained in mice which were both pre-conditioned and post-conditioned with MRF. Preferably said post-conditioning takes place, at least 24 hours after total body irradiation. In such instance pre-conditioning can even be dispensed with. More generally transplantation of any tissue or cells to be grafted into a host should take place not earlier than at least 24 hours after body irradiation.

It has been further found that MRF counteracts the accelerating effect induced by T-lymphocytes, particularly of spleen cells, on graft rejection.

Bone marrow transplanted from a same animal into one having a genetic deficiency of the immune system is capable of overcoming the disease liable of being induced in the latter animal.

TABLE 9

This table reports the results obtained under similar conditions, yet with semi-compatible donor/recipient strain combination. No pre-conditioning is needed for induction of chimerism. In this experiment, full success has been obtained with injection of MRF and BM cells after irradiation only, and permanent chimerism is demonstrates a by hemoglobin pattern for all of the surviving animals.

3° Toxicity study 5 mg dose of MRF has been injected into each of 100 mice. No toxic effect has been observed.

Repeated daily injections of 2 mg over a period of 1 month have not produced any evidence of toxicity. Animals were in perfect condition. They developped normally with no symptoms of disease. The product was very well tolerated.

The possible induction of chimerism by the biological fraction according to the invention, with an even greater rate of success than that which is shown in the tables, when the experiments are carried out with animals recipient under more sterile conditions, coupled with the great tolerance which it shows in vivo, thus are capable of providing a new therapeutic and experimental basis for the control of HVG reaction or GVH reaction in bone marrow transplantation. Its practical application in organ- and bone marrow transplantation, in auto-immune disease and in the immunotherapy of cancer, for instance leukemia and breast cancer, are but a few of the most compelling areas of its application.

The invention is thus concerned with the pharmaceutical compositions containing said fraction in dosage unit form associated with classical pharmaceutical vehicles suitable for any appropriate form of administration. Particularly it relates to injectable, sterile solutions, at a pH not lower than 7, preferably from about 7.2 to about 7.6, containing effective doses of said fraction. Particularly it relates also to lyophilized fractions, or lyophilized preparations containing said fractions in association with a vehicle so selected as to enable the extemporaneous formation of such solutions at a pH ranging from about 7.2 to about 7.6, by the addition thereto of an injectable volume of either sterile water or any appropriate physiological liquid vehicle.

The invention is also concerned with the biological standard reactants which can be formed with the MRF fraction, particularly, as a means for enabling comparative assessments of the activities of other tested preparations with respect to the control of acquired immunity, bone marrow reconstitution or protection with respect to radiation.

The invention finally consists of a method for grafting heterologous tissue or cells into a host which comprises destroying the host's immune defenses, such as by irradiation, treating said host with an efficient dose of MRF as well as casing said graft thereafter, preferably at 24 hours after the destruction of the host's immune defenses.

TABLE 1

LACK OF SPECIES SPECIFICITY OF SN AND INFLUENCE OF PH ON INCORPORATION OF $^3$H—THYMIDINE BY MOUSE BM CELLS IN THE PRESENCE OF MRF

| | Incubation hours | | | |
|---|---|---|---|---|
| Code | ½ hour CPM ± S.O. | 4 hours CPM ± S.O. | pH | Sample (3×) |
| 1 | 10 301 ± 280 | 12 377 ± 856 | 6.2–6.4 | $10^6$ mouse BM cells in TC 199 |
| 2 | 8 880 ± 244 | 11 109 ± 1 477 | 7.0–7.2 | " |
| 3 | 8 313 ± 403 | 13 783 ± 1 464 | 7.6–7.8 | " |
| 4 | 9 199 ± 1 158 | 13 722 ± 650 | 6.2–6.4 | $10^6$ mouse BM cells in SN-MRF |
| 5 | 10 373 ± 639 | 19 532 ± 1 502 | 7.0–7.2 | " |
| 6 | 13 974 ± 1 134 | 24 316 ± 198 | 7.6–7.8 | " |
| 7 | 11 759 ± 1 070 | 27 318 ± 3 660 | 7.0–7.2 | $10^6$ rat BM cells in SN-MRF |
| 8 | 7 249 ± 490 | 8 351 ± 895 | 7.0–7.2 | $10^6$ rat BM cells in TC 199 |

Donors of BM cells: C57BL/6 mice, M, adult or Cara rats, M, young (100 g body weight)
Cellular concentration of samples: $10^6$ BM cells/ml
Donors of supernatant: young Cara rats, M, (100 g body weight), SN-MRF = $50.10^6$ BM cells/ml
Ratio SN/mouse (or rat) BM cells: 20/1 (SN resulting from $20.10^6$ rat cells)
Medium: TC 199
Labelling: $^3$H—thymidine, 2 µCi/0.1 ml/sample

TABLE 2

ACTION OF WHOLE RABBIT BONE MARROW SUPERNATANT (SN) ON $^3$H—THYMIDINE INCORPORATION BY MOUSE BONE MARROW CELLS IN VITRO

| | Time of incubation (Hours) | | | | | |
|---|---|---|---|---|---|---|
| | 1 cpm | 1.5 cpm | 2 cpm | 3 cpm | 4 cpm | |
| 1 | 7 990 ± 1 231 | 14 182 ± 1 769 | 13 270 ± 1 274 | 57 090 ± 4 463 | 80 933 ± 7 179 | $2 \times 10^6$ BM cells in Rab-SN |
| 2 | 10 164 ± 1 824 | 10 436 ± 1 318 | 29 967 ± 2 771 | 81 790 ± 3 756 | 100 679 ± 8 583 | $2 \times 10^6$ BM cells in $0.1°/_{oo}$ BSA |
| 3 | 8 037 ± 554 | 11 053 ± 1 686 | 30 919 ± 1 550 | 79 696 ± 1 471 | 115 297 ± 7 901 | $2 \times 10^6$ BM cells in TC 199 |

Donors of BM cells: C57BL/6-M-adult ($2.10^6$ BM Cells/ml)
SN: rabbit bone marrow supernatant in an amount corresponding to $50.10^6$ BM cells/ml
Ratio: MRF/BM cells: 5/1
Labelling with $^3$H—thymidine, 2 µCi/0.1 ml/sample
Medium: TC 199, pH 7.5
BSA: bovine serum albumin

TABLE 3

AN ULTRAFILTRATION FRACTION OF MW > 100,000 FROM BONE MARROW SUPERNATANT STIMULATES $^3$H—THYMIDINE INCORPORATION BY BONE MARROW CELLS IN VITRO - THE FRACTION OF MW < 30,000 INHIBITS INCORPORATION

| | Incubation (hours) | | | |
|---|---|---|---|---|
| Code | 1 h cpm ± s.d. | 2 h cpm ± s.d. | 3 h cpm ± s.d. | |
| 1 | 31 185 ± 4 311 | 73 180 ± 6 972 | 126 631 ± 7 842 | $2 \times 10^6$ BM cells + 200 µg fraction MW > 100.000 |
| 2 | 18 008 ± 1 152 | 19 347 ± 2 059 | 37 868 ± 4 478 | $2 \times 10^6$ BM cells + 200 µg fraction MW < 30.000 |
| 3 | 35 064 ± 2 841 | 62 392 ± 5 909 | 98 586 ± 2 901 | $2 \times 10^6$ BM cells + 200 µg fraction MW > 30.000 |
| 4 | 23 327 ± 2 814 | 32 420 ± 4 705 | 49 918 ± 6 752 | $2 \times 10^6$ BM cells + 200 µg fraction MW < 100.000 |
| 5 | 20 265 ± 4 294 | 35 049 ± 5 626 | 65 291 ± 8 203 | $2 \times 10^6$ BM cells in TC 199 |

Donors of bone marrow (BM) cells were C57BL/6 mice ($2 \times 10^6$ BM cells/ml). The incubation medium was TC 199, pH 7.5
2 µCi/0.1 ml $^3$H—thymidine were added to each tube. Samples were in triplicate.
s.d.: standard deviation

TABLE 4

INFLUENCE OF MRF HEATING ON THE $^3$H—THYMIDINE INCORPORATION BY THE ULTRAFILTRATED MRF FRACTION ABOVE 100,000

| | Incubation (hours) | | | |
|---|---|---|---|---|
| Code | 1 h cpm | 2 h cpm | 3 h cpm | |
| 1 | 21 906 ± 2 393 | 33 277 ± 4 738 | 75 795 ± 11 017 | $2 \times 10^6$ BM cells + 200 µg "MW > 100,000" |
| 2 | 15 111 ± 408 | 28 595 ± 3 274 | 56 483 ± 8 390 | $2 \times 10^6$ BM cells + 200 µg same, however after heating at 70° C. for 30 mn |
| 3 | 14 267 ± 1 693 | 31 353 ± 7 612 | 36 418 ± 4 828 | $2 \times 10^6$ BM cells in TC 199 |

Donors of BM cells: C57BL/mice ($2.10^6$ BM cells/ml)
Rabbit MRF fraction
Medium: TC 199, pH 7.5
Labelling with $^3$H—thymidine, 2 µCi/0.1 ml/sample

TABLE 5

ACTION OF ULTRA FILTRATED MFR ABOVE 100,000 ON $^3$H—THYMIDINE INCORPORATION IN VITRO - COMPARISON WITH FRACTIONS BELOW 100,000

| Code | 1 h cpm | 2 h cpm | 3 h cpm | Incubation (hours) |
|---|---|---|---|---|
| 1 | 29 510 ± 748 | 81 814 ± 1 730 | 93 896 ± 10 605 | 2 × 10$^6$ BM cells + 200 μg of "MW > 100,000" |
| 2 | 19 744 ± 1 961 | 24 078 ± 3 511 | 29 500 ± 2 332 | 2 × 10$^6$ BM cells + 200 μg of "MW > 30,000" |
| 3 | 18 893 ± 314 | 22 567 ± 2 378 | 47 168 ± 3 561 | 2 × 10$^6$ BM cells + 200 μg of "MW < 30,000" |
| 4 | 19 834 ± 3 576 | 62 750 ± 3 384 | 47 938 ± 3 146 | 2 × 10$^6$ BM cells in TC 199 |

Donors of BM cells: C57BL/6-adult mice (2.10$^6$ BM cells/ml)
Rabbit MRF fraction
Medium: TC 199, pH 7.5
Labelling with $^3$H—thymidine, 2 μCi/0.1 ml/sample

TABLE 6

IN VIVO EFFECTS OF ULTRAFILTRATED MRF FRACTION ABOVE 100,000 ON $^3$H—THYMIDINE INCORPORATION BY MOUSE BONE MARROW

| GROUPS 5 mice/group | Injection (0.5 ml in vivo) | Test time (H after injection) | cpm (2 × 10$^6$ BM cells) |
|---|---|---|---|
| 1a | 1 mg of "MW > 100,000" + 4 μCi of thymidine | 1 hour | 157 ± 22 |
| 1b | 1 mg of "MW > 100,000 H" + 4 μCi of thymidine | 1 hour | 100 ± 12 |

Donors of BM cells: C57BL/6-mice (2.10$^6$ BM cells/ml)
Rabbit MRF fraction
"MW > 100,000 H" is "MW > 100,000" after heating at 70° C. for 30 minutes
Treatment: 1 mg of fraction + 4 μCi of thymidine in 0.5 ml
Medium: saline, pH 7.5

TABLE 7

IN VIVO EFFECTS OF ULTRAFILTRATED MRF FRACTION ABOVE 100,000 ON $^3$H—THYMIDINE INCORPORATION BY BONE MARROW CELLS

| Groups 5 mice/group | Injection (0.1 ml in vivo) | Test time (H after injection) | cmp x (2 × 10$^6$ BM cells) |
|---|---|---|---|
| 1a | 500 μg of "MW > 100,000" + 2 μCi of thymidine | 1 hour | 60 ± 8 |
| 1b | 500 μg of BSA + 2 μCi of thymidine | 1 hour | 44 ± 8 |
| 2a | 500 μg of "MW > 100,000" + 2 μCi of thymidine | 2 hours | 54 ± 6 |
| 2b | 500 μg of BSA + 2 μCi of thymidine | 2 hours | 44 ± 9 | x Figures represent the mean value for the 5 animals of the group, each in duplicate
Donors: C57BL/6-M-adult
Rabbit MRF fraction
Treatment: 500 μg of fraction + 2 μCi of thymidine in 0.1 ml, i.v.
BSA: bovine serum albumine
Medium: saline, pH 7.5

TABLE 9

BONE MARROW TRANSPLANTATION OF MRF IN HYBRID RECIPIENT MICE

| Animals | | TBI | | Post-conditioning | | | Survival at 6 months | Chimerism |
|---|---|---|---|---|---|---|---|---|
| Group | No | rads | h+ | Product | No of BM cells | Route | | |
| A | 10 | 900 | 24 | 3 mg MRF | 35 × 10$^6$ | i.v. | 9 (90%) | 9 (100%) |
| B | 40 | | 24 | — | 35 × 10$^6$ | i.v. | 8 (20%) | 0 (0%) |

TBI: total body irradiation. MRF: marrow regulating factor; Amicon Diaflo membrane ultrafiltration fraction (MW 100,000) of supernatant of rabbit bone marrow cells. Donors of bone marrow were adult C57BL/6 mice, recipients were F1 hybrid, 3–4 month-old C57BL/6 × A/J female mice. The parenteral bone marrow cells were washed once and then suspended in TC 199 containing the MRF immediately before inoculation. The cells were inoculated 24 hours after TBI. Chimerism was assessed by individual hemoglobin typing in each surviving recipient hybrid mouse.

We claim:

1. A water-soluble biologically active extract of bone marrow wherein said extract is identified by being substantially free of components having a molecular weight lower than that at least about 30,000; possessing an ultra-violet spectra having a peak of absorption at 280 mu; is capable of stimulating incorporation of H-thymidin bone marrow cells in vitro and in vivo; is capable of being lyophilized, and is capable of being deactivated by heating at about 70° C. for about thirty minutes, whereby said extract is capable of exhibiting biological activity in the form of a solution having a pH of at least 7 and controlling the immune reactions of a host against allogenic cells or tissue.

2. The extract according to claim 1 which possesses a biological activity that is non-species-specific.

3. The extract according to claim 1 which is free of components having a molecular weight lower than about 100,000.

4. The extract according to claim 1 which is a lyophiliate.

TABLE 8

ALLOGENEIC BONE MARROW TRANSPLANTATION IN VIVO WITH MARROW REGULATING FACTOR (MRF)

| Animals | | | | Pre-conditioning | | | TBI Dose (rads) | | Post-conditioning | | | Survival at 6 months after TBI | Chimerism |
|---|---|---|---|---|---|---|---|---|---|---|---|---|---|
| Group | No | Age (mths) | Sex | Product | route | h− | | h+ | Product | No of BM cells (× 10$^6$) | Route | | |
| A | 10 | 3–4 | M | 5 mg MRF | i.v. | 1.5 | 850 | 24 | 3 mg MRF | 37 | i.v. | 6 (60%) | 6 (100%) |
| B | 10 | 3–4 | M | 2.5 mg MRF | i.v. | 1.5 | 850 | 24 | 3 mg MRF | 37 | i.v. | 5 (50%) | 5 (100%) |
| C | 10 | 3–4 | M | 1.0 mg MRF | i.v. | 1.5 | 850 | 24 | 3 mg MRF | 37 | i.v. | 4 (40%) | 4 (100%) |
| D | 10 | 3–4 | M | TC 199 | i.v. | 1.5 | 850 | 24 | 3 mg MRF | 37 | i.v. | 9 (90%) | 0 (0%) |
| E | 20 | 3–4 | M | TC 199 | i.v. | 1.5 | 850 | 24 | | 37 | i.v. | 0 | |

TBI: total body irradiation. MRF: marrow regulating factor; Amicon Diaflo membrane ultrafiltration fraction (MW > 100,000) of supernatant of rabbit bone marrow cells. Donors of bone marrow were adult DBA/2 female mice, recipients were 3–4 month-old male C57BL/6 mice. MRF or TC 199 were injected 1.5 h before TBI (h−). The allogeneic bone marrow cells were washed once and then suspended in TC 199 containing the MRF immediately before inoculation. The cells were inoculated 24 h (h+) after TBI. Chimerism was assessed by hemoglobin typing and skin grafting of the individual surviving recipients (4). For the cause of mortality in groups A, B and C, see results section.

5. The extract according to claim 1 which permits the engraftment of allogenic bone marrow and induces persistent chimerism in previously lethally irradiated animals.

6. The extract according to claim 1 wherein the pH is about 7.2 to about 7.6.

7. The extract according to claim 1 in which said extract is derived from the physiological inter-cellular medium of the bone marrow of animals.

8. A method of treating a host against immune reactions of allogenic cells or tissue which comprises administering to said host an effective amount of the extract of claim 1 in a pharmaceutically acceptable carrier.

9. The method of claim 8 wherein said extract is in saline solution.

10. The method of claim 8 wherein the administration is of the extract, which is buffered.

11. A method of treating mammals against the effects of irradiation which comprises administering to a mammal an effective amount of the extract of claim 1 in a pharmaceutically acceptable carrier.

12. A method of treating mammals so as to promote engraftment of allogenic marrow which comprise administering to a mammal an effective amount of the extract by any one of claims 1, 2 or 3 in a pharmaceutically acceptable carrier.

13. A method of transplanting bone marrow or skin between at least a partially genetically incompatible donor and a recipient which comprise administering to said recipient an effective amount of the extract of any one of claims 1, 2 or 3 in a pharmaceutically acceptable carrier prior to transplant.

14. The method of claim 13 including the steps of irradiating said recipient after treatment with said extract and before transplant and then further administering an effective amount of said extract after transplant.

15. A method for grafting heterologous tissue or cells into a host which comprises the steps of
 (a) destroying the immune defenses of said host,
 (b) grafting said tissue or cells into said host, and
 (c) administering to said host an effective amount of the extract of any one of claims 1, 2 or 3 in a pharmaceutically acceptable carrier.

16. The method of claim 15 wherein said extract is administered at least prior to grafting.

17. A therapeutic composition for treating a host against immune reactions of allogenic cells or tissue comprising an effective amount of the extract of any one of claims 1, 2 or 3 and a pharmaceutically acceptable carrier.

18. The composition of claim 17 wherein said carrier is a saline solution.

19. The composition of claim 17 which is buffered so as to be at a pH of about 7.2 to about 7.6.

20. The composition of claim 17 wherein said extract is a lyophilate.

21. A therapeutic composition for protecting mammals against irradiation which comprises an effective amount of the extract of any one of claims 1, 2 or 3 and a pharmaceutically acceptable carrier.

22. A therapeutic composition for promoting grafting of heterologous tissue or cells into a host which comprises an effective amount of the extract of any one of claims 1, 2, or 3 and a pharmaceutically acceptable carrier.

23. A process for the preparation of water-soluble biologically active extract from bone marrow capable of controlling the immune reactants of a host against allogenic cells or tissue, which comprises the steps of:
 (a) collecting physiological inter-cellular medium from bone marrow cells;
 (b) filtering and separating from said inter-cellular medium components having a molecular weight lower than at least about 30,000; and
 (c) recovering the biologically active portion free from said components having a molecular weight below at least about 30,000;
 said medium being maintained at a pH of at least about 7.0.

24. The process of claim 23 wherein the pH is from about 7.2 to about 7.6.

25. The process of claim 23 in which said inter-cellular medium is from the bone marrow of animals.

26. The process of claim 23 wherein said inter-cellular medium from bone marrow of step (a) is suspended in a physiological solution.

27. The process of claim 26 wherein said physiological solution is a saline solution.

28. The process of claim 26 wherein said physiological solution is buffered.

29. The process of claim 28 wherein said physiological solution is buffered with a buffer selected from the group consisting of Hank's medium and Earle's medium.

30. The process of claim 23 wherein said process is carried out below ambient temperature.

31. The process of claim 30 wherein the temperature is between 0° and 5° C.

32. The process of claim 23 in which components having a molecular weight of less than 100,000 are separated from said extract.

33. The process of claim 23 in which step (b) is carried out with a microporous filter.

34. The process of claim 23 wherein step (b) includes centrifuging said extract at below ambient temperature.

35. The process of claim 23 including the step of removing organ specific antigens and non-extract related anti-bodies.

* * * * *